United States Patent [19]

Ohtsubo et al.

[11] Patent Number: 4,900,551
[45] Date of Patent: Feb. 13, 1990

[54] METHOD FOR PREVENTING TERMITES AND MICROENCAPSULATED ORGANOPHOSPHORUS TERMITE CONTROLLING COMPOSITION

[75] Inventors: Toshiro Ohtsubo, Osaka; Shigenori Tsuda, Kyoto; Yukio Manabe, Osaka; Takaaki Itoh, Hyogo; Hitoshi Kawada; Goro Shinjo, both of Osaka; Kozo Tsuji, Nara, all of Japan

[73] Assignee: Sumitomo Chemical Company, Ltd., Osaka, Japan

[21] Appl. No.: 166,346

[22] Filed: Mar. 10, 1988

Related U.S. Application Data

[63] Continuation-in-part of Ser. No. 1,113, Jan. 7, 1987, abandoned.

[30] Foreign Application Priority Data

Jan. 7, 1986 [JP] Japan ................................. 61-1912
Feb. 17, 1986 [JP] Japan ................................. 61-32647

[51] Int. Cl.$^4$ ..................... A01N 25/28; A01N 57/14; B01J 13/02
[52] U.S. Cl. .................................... 424/408; 264/4.7; 424/419; 424/DIG. 11; 428/402.21; 514/132
[58] Field of Search ................... 428/402.21; 424/408, 424/419, DIG. 11

[56] References Cited

U.S. PATENT DOCUMENTS

| | | | |
|---|---|---|---|
| 3,208,951 | 9/1965 | Berger et al. | 264/4.7 |
| 3,429,827 | 2/1969 | Ruus | 264/4.7 |
| 3,466,353 | 9/1969 | Turner | 264/53 |
| 3,858,346 | 1/1975 | Bailey | 424/84 X |
| 4,285,720 | 8/1981 | Scher | 71/88 |
| 4,456,569 | 6/1984 | Rodson et al. | 264/4.7 X |
| 4,557,755 | 12/1985 | Takahashi et al. | 71/100 |

FOREIGN PATENT DOCUMENTS

58-144304 8/1983 Japan.

*Primary Examiner*—Richard D. Lovering
*Attorney, Agent, or Firm*—Sughrue, Mion, Zinn, Macpeak & Seas

[57] ABSTRACT

Termites are prevented by applying thereto microencapsulated organophosphorus termite controlling composition in an amount of 5–100 g as an effective ingredient. The composition comprises an organophosphorus insecticidal compound encapsulated in a microcapsule formed of a polyurea or polyurethane wall and having an average particle diameter of not more than 80 $\mu$m, a wall thickness of 0.1–1 $\mu$m, and a value of the average particle diameter/wall thickness of 20–400.

9 Claims, No Drawings

METHOD FOR PREVENTING TERMITES AND MICROENCAPSULATED ORGANOPHOSPHORUS TERMITE CONTROLLING COMPOSITION

This is a continuation-in-part of application Ser. No. 001,113, filed Jan. 7, 1987 and now abandoned.

The present invention relates to a method for preventing termites and a microcapsulated organophosphorus termite controlling composition used therefor.

In general, organophosphorus insecticides have excellent activities immediately after they are spread, but many of them tend to be quickly decomposed and dissipated once they have been spread in the environment. Accordingly, when a residual effect is necessitated, their use may be limited. Thus, at present in the field of prevention and extermination of termites, organophosphorus insecticides cannot be used; thus the organochlorine compounds such as chlordane, lindane, dieldrin, etc. are mainly used. However, these organochlorine compounds, while displaying high effects over an extended period of time against the termites, involve an environmental pollution problem. Therefore, their uses are being gradually restricted. Under such circumstances, development of a substitute is being desired. Thus, it is necessary to develop an insecticidal composition made by the use of an insecticide such as an organophosphorus insecticide which rapidly decomposes and dissipates in the environment and yet has an excellent residual effect.

Generally, since the active ingredient contained in a microcapsule is isolated from the external environment by a membrane substance, its decomposition, volatization, etc. are restricted, with the result that its dissipation is restrained.

By utilizing this characteristic property, there comes to be a possibility of applying an organophosphorus insecticidal composition to termite control which has a practical residual effect to some extent.

With this in view, the present inventors conducted repeated studies on the microencapsulated organophosphorus termite controlling composition, and confirmed that by encapsulating the active ingredient the residual effect of the composition is certainly improved. However, when various factors constituting the microcapsule composition, especially the particle size and the wall thickness, varied, there were frequently seen the differences in the effect, even when the same active ingredient was encapsulated. In other words, in order to develop a microencapsulated termite controlling composition which displays a sufficient residual effect, it has been found necessary to develop optimum conditions for the particle diameter and the wall thickness of the microcapsule.

The present inventors have made strenuous studies on the conditions which would show particularly excellent residual effect against termites in encapsulating the organophosphorus termite controlling compound in a microcapsule of polyurethane wall or polyurea wall. As a result, they have found out that, irrespective of the case of encapsulating in a microcapsule with a polyurethane wall or with a polyurea wall, when the microcapsule is so controlled as to have an average particle diameter of not more than 80 μm, a wall thickness of 0.1–1 μm, and a value of the average particle diameter/wall thickness of 20–400, the composition should show particularly excellent residual effect with facility of handling.

The present composition, diluted with water, if necessary is applied in an amount of 5–100 g, preferably 20–40 g, per m$^2$, to a soil surface under a floor of a building, a foundation, pebble stones, etc. The composition may be applied by a ladle or a conventional sprayer for emulsion.

Above all, the present inventors have confirmed that, when O,O-dimethyl-O-(3-methyl-4-nitrophenyl)phosphorothioate (hereinafter to be referred to as fenitrothion) is used as an active ingredient of the organophosphorus termite controlling composition, a microcapsule composition which shows particularly excellent residual effect against the termites can be obtained.

As the method of microencapsulation with either a polyurethane wall or a polyurea wall, it is recommended as a convenient method to employ an interfacial polymerization method using a polyfunctional isocyanate compound.

That is to say, in case of encapsulating an organophosphorus insecticidal compound in a polyurethane wall:

(1) A solution containing at least one of the organophosphorus insecticidal compounds and a polyfunctional isocyanate compound having at least two isocyanate groups therein is dispersed into an aqueous solution containing a dispersing agent and a polyhydric alcohol having at least two hydroxyl groups therein, and then the resulting dispersion is subjected to an interfacial polymerization reaction, or (2) A solution containing at least one of the organophosphorus insecticidal compounds and a polyfunctional isocyanate compound having at least two isocyanate groups therein is dispersed into an aqueous solution containing a dispersing agent, and then the dispersion is subjected to an interfacial polymerization reaction by adding a polyhydric alcohol having at least two hydroxyl groups therein.

Alternatively, in case of encapsulating an organophosphorus insecticidal compound in a polyurea wall:

(1) A solution containing at least one of the organophosphorus insecticidal compounds and a polyfunctional isocyanate compound having at least two isocyanate groups therein is dispersed in to an aqueous solution containing a dispersing agent with or without a polyfunctional amine having at least two amino groups therein, and then the resulting dispersion is subjected to an interfacial polymerization reaction, or (2) A solution containing at least one of the organophosphorus insecticidal compounds and a polyfunctional isocyanate compound having at least two isocyanate groups therein is dispersed into an aqueous solution containing a dispersing agent, and the dispersion is subjected to an interfacial polymerization reaction by adding a polyfunctional amine having at least two amino groups therein.

After the encapsulation reaction, the resulting suspension of the microencapsulated product may be offered as such for practical use or be used after diluting with water. Practically, it is preferred to add a thickening to the suspension or the diluted suspension to use the resultant as a stabilized slurry type composition.

When an excessive amount of the amine is used in the polymerization, the reaction product may be neutralized with an acid, e.g., hydrochloric acid, after the reaction.

The microencapsulation reaction is preferably carried out under heating. When the heating temperature is too low, the reaction rate becomes slow, and when the temperature is too high, there arises a possibility for the active ingredient to be decomposed during the encapsulation process. Accordingly, it is preferred to keep the heating temperature in the range of about 40° C. to 80° C.

The reaction period, though variable depending on the temperature, is usually preferred to be more than 1 hour.

In dispersing the solution containing at least one of the organophosphorus insecticidal compounds and a polyfunctional isocyanate compound having at least two isocyanate groups therein (hereinafter to be referred to as oil phase) in an aqueous solution containing a dispersing agent with or without others (hereinafter to be referred to as aqueous phase), any one of the batch type dispersing apparatus and the continuous feed type dispersing apparatus may be used, but the ratio of the oil phase to the aqueous phase in dispersing is preferably not more than 2, at most, of the former to 1 of the latter. When the amount of the oil phase exceeds the above value, there arises a danger for the water-in-oil type dispersion system to be obtained instead of the oil-in-water type dispersion which is necessary for the present microencapsulation reaction.

Assuming the amount of the polyfunctional isocyanate compound to be charged in the oil phase in the production to be $W_{NCO}$ parts by weight, the molecular weight thereof to be $M_{NCO}$, and the number of the isocyanate groups contained in a molecule to be $N_{NCO}$, then, in effecting a microencapsulation reaction with a polyurethane wall by the use of a polyhydric alcohol having a molecular weight of $M_{OH}$ and the number of the hydroxyl groups contained in a molecule of $N_{OH}$, it is necessary to add a polyhydric alcohol having at least:

$$\frac{W_{NCO} \cdot N_{NCO}}{M_{NCO}} \times \frac{M_{OH}}{N_{OH}} \text{ parts by weight.}$$

Alternatively, in effecting a microencapsulation reaction with a polyurea wall by the use of a polyfunctional amine having the molecular weight of $M_{NH2}$ and the number of the amino groups $N_{NH2}$ contained in one molecule; it is necessary to add a polyfunctional amine of at least:

$$\frac{W_{NCO} \cdot N_{NCO}}{M_{NCO}} \times \frac{M_{NH2}}{N_{NH2}} \text{ parts by weight.}$$

In case of reacting the polyfunctional isocyanate with water to form a polyurea wall, usually there is no specific problem if there is an amount of water sufficient to disperse the oil phase.

The wall thickness (T) of the microcapsule can be approximately expressed by the following equation (I), wherein the average particle diameter is d, the amount of the core substance is $W_C$ parts by weight, the amount of the wall substance is $W_W$ parts by weight, the density of the core substance is $\rho_c$, and the density of the wall substance is $\rho_W$, respectively.

Proximate equation (I):

$$\text{Wall thickness } (T) = \frac{W_W}{W_C} \cdot \frac{\rho_c}{\rho_W} \cdot \frac{d}{6}$$

Assuming the amount of the oil phase to be charged in production to be $W_{oil}$, $W_C$ is expressed in the proximate equation (I) as: $W_C = W_{oil} - W_{NCO}$.

$W_W$ is expressed by the following equations, respectively:

(1) In case of forming a polyurethane wall by the reaction of a polyfunctional isocyanate with a polyhydric alcohol, $$W_W = W_{NCO} + \frac{W_{NCO} \cdot N_{NCO}}{M_{NCO}} \cdot \frac{M_{OH}}{N_{OH}}$$

(2) In case of forming a polyurea wall by the reaction of a polyfunctional isocyanate with a polyfunctional amine, $$W_W = W_{NCO} + \frac{W_{NCO} \cdot N_{NCO}}{M_{NCO}} \cdot \frac{M_{NH2}}{N_{NH2}}$$

(3) In case of forming a polyurea wall by the reaction of a polyfunctional isocyanate with water, because 2 moles of isocyanate group react with 1 mole of $H_2O$ to form 1 of urea bond to generate 1 mole of $CO_2$, assuming the molecular weight of $H_2O$ to be 18 and that of $CO_2$ to be 44, $$W_W = W_{NCO} + \frac{W_{NCO} \cdot N_{NCO}}{M_{NCO}} \cdot \frac{(18 - 44)}{2}$$

Accordingly, the proximate equations (I) are as follows:

(1) In case of forming a polyurethane wall by the reaction of a polyfunctional isocyanate with a polyhydric alcohol, Proximate equation (II):

Wall thickness $(T_1) =$ $$\frac{W_{NCO}\left(1 + \frac{N_{NCO} \cdot M_{OH}}{M_{NCO} \cdot N_{OH}}\right)}{W_{oil} - W_{NCO}} \cdot \frac{\rho_c}{\rho_W} \cdot \frac{d}{6}$$

(2) In case of forming a polyurea wall by the reaction of a polyfunctional isocyanate with polyfunctional amine, Proximate equation (III):

Wall thickness $(T_2) =$ $$\frac{W_{NCO}\left(1 + \frac{N_{NCO} \cdot M_{NH2}}{M_{NCO} \cdot N_{NH2}}\right)}{W_{oil} - W_{NCO}} \cdot \frac{\rho_c}{\rho_W} \cdot \frac{d}{6}$$

(3) In case of forming a polyurea wall by the reaction of a polyfunctional isocyanate with water, Proximate equation (IV):

$$\text{Wall thickness } (T_3) = \frac{W_{NCO}\left(1 - \frac{13 \cdot N_{NCO}}{M_{NCO}}\right)}{W_{oil} - W_{NCO}} \cdot \frac{\rho_c}{\rho_W} \cdot \frac{d}{6}$$

The wall thickness herein referred to is basically what has been calculated by the use of the proximate equation (II), (III), or (IV).

Accordingly, in order to produce a microcapsule having the wall thickness of 0.1–1 μm and the value of the average particle diameter/wall thickness of 20–400, the production conditions may be so determined as to satisfy the following equations:

(1) In case of forming a polyurethane wall by the reaction of a polyisocyanate compound with a polyhydric alcohol, 0.1 μm $\leq T_1 \leq$ 1 μm and yet, 20 $\leq$ d/T$_1$ $\leq$ 400.

(2) In case of forming a polyurea wall by the reaction of a polyfunctional isocyanate compound with a polyfunctional amine, 0.1 μm $\leq T_2 \leq$ 1 μm and yet, 20 $\leq$ d/T$_2$ $\leq$ 400.

(3) In case of forming a polyurea wall by the reaction of a polyfunctional isocyanate with water, 0.1 μm $\leq T_3 \leq$ 1 μm and yet, 20 $\leq$ d/T$_3$ $\leq$ 400.

The average particle diameter of the microcapsule is mainly determined by the kind and concentration of the dispersing agent used in dispersion and the intensity of mechanical stirring in dispersion. For determining the average particle diameter, there may be used, for example, a Coulter counter Model TA-II (available from Nikkaki).

Examples of the polyfunctional isocyanate compounds are toluene diisocyanate, hexamethylene diisocyanate, an adduct of toluene diisocyanate with trimethylolpropane, a self-condensate of hexamethylene diisocyanate, and SUMIDUR L ® (made by Sumitomo-Bayer Urethane Co., Ltd.), SUMIDUR N ® (made by Sumitomo-Bayer Urethane Co., Ltd.), etc.

Examples of the polyhydric alcohols having two or more OH groups are generally ethylene glycol, propylene glycol, butylene glycol, hexanediol, heptanediol, dipropylene glycol, triethylene glycol, glycerin, resorcinol, hydroquinone, etc.

Examples of the polyfunctional amines having two or more NH$_2$ groups are ethylenediamine, hexamethylenediamine, phenylenediamine, toluenediamine, diethylenetriamine, etc.

On the other hand, with respect to the composition of the hydrophobic liquid, namely, the oil phase, a mixture of the polyfunctional isocyanate compound and the organophosphorus insecticidal compound may be directly used, if these two compounds are cosolubilizable, but when these two compounds are not cosolubilizable or when one of the compounds is a solid, it is desirable to select an organic solvent which is hardly miscible with water and yet can dissolve the polyfunctional isocyanate compound and the organophosphorus insecticide and use an even mixture of the three compounds (polyfunctional isocyanate compound, organophosphorus insecticide and the solvent). The organic solvent to be used for this purpose may be selected from, for example, ordinary organic solvents of hydrocarbon (e.g., xylene, toluene, alkylbenzene, phenyl xylyl ethane, hexane, heptane, etc.), chlorinated hydrocarbons (e.g., chloroform), ketones (e.g., methyl ethyl ketone, cyclohexanone, etc.), and esters (e.g., diethyl phthalate, n-butyl acetate, etc.).

As to the dispersing agents, there may be used, for example, natural polysaccharides (e.g., gum arabic), semisynthetic polysaccharides (e.g., carboxymethylcellulose, methylcellulose, etc.), synthetic water-soluble polymers (e.g., polyvinyl alcohol), fine powders of minerals such as magnesium aluminium silicate, etc. either solely or as a mixture of two or more. When the dispersibility is weak, the dispersibility may be improved by adding a known surfactant such as given in H. Horiguchi; "Synthetic Surface Active Agent". As to the suspension stabilizer for the microcapsule slurry, it may be possible to use the water-soluble polymers enumerated above as dispersing agent as such, but according to necessity, natural polysaccharides (e.g., xanthan gum, locust bean gum, etc.), semi-synthetic polysaccharides (e.g., carboxymethylcellulose), synthetic polymers (e.g., sodium polyacrylate), fine powders of minerals such as magnesium aluminium silicate, etc. may be used either solely or in combination of two or more as a thickening agent.

Specific examples of the organophosphorus insecticides are:

fenitrothion,

O,O-dimethyl-O-(4-cyanophenyl)phosphorothioate (hereinafter to be referred to as cyanophos), 2-methoxy-4H-1,3,2-benzodioxaphosphorin-2-sulfide (hereinafter to be referred to as salithion), O,O-diethyl(O-2-isopropyl-6-methylpyrimidin-4-yl) phosphorothioate (hereinafter to be referred to as diazinon), O,O-diethyl O-3,5,6-trichloro-2-pyridylphosphorothioate (hereinafter to be referred to as chlorpyrifos), O,O-diethyl α-cyanobenzylideneamino-oxyphosphonothioate (hereinafter to be referred to as phoxim), (E)-O-2-isopropoxycarbonyl-1-methylvinyl O-methylethylphosphoramidothioate (hereinafter to be referred to as protamphos), O,O-diethyl 2,3-dihydro-3-oxo-2-phenyl-6-pyridazinyl phosphorothioate (hereinafter to be referred to as pyridaphenthion), O-[trans-2-chloro-1-(2,4,5-trichlorophenyl)vinyl]O,O-dimethyl phosphate (hereinafter to be referred to as Tetrachlorvinphos), O-[2-chloro-1-(2,4-dichlorophenyl)vinyl]O,O-dimethyl phosphate (hereinafter to be referred to as dimethylvinphos), etc.

The present invention is illustrated in further detail by way of the following Examples, Comparative Examples and Test Examples.

EXAMPLE 1

SUMIDUR L ® (as aforesaid) (12 g) was added to fenitrothion (200 g), and the mixture was stirred to make an even solution, which was added to an aqueous solution (350 g) containing a 5 wt. % gum arabic as a dispersing agent to agitate the mixture at room temperature for several minutes until it became microdrops with T. K. Autohomomixer (trade name of Tokushukika Kogyo K.K.). The revolution was 1800 r.p.m. Then, after adding an ethylene glycol (6 g) to the dispersion, the mixture was allowed to react in a constant temperature bath at 60° C. for 24 hours while slowly stirring to produce a suspension of microencapsulated product. Water was added thereto to adjust the whole weight to 1000 g to give a fenitrothion microcapsule slurry having the active ingredient concentration of 20 wt. %. (Composition 1-1).

The resulting microcapsules having polyurethane wall had an average particle diameter of 80 μm, a wall thickness of 0.67 μm, and a value of the average particle diameter/wall thickness of 119.

EXAMPLE 2

Except that the amount of SUMIDUR L ® (as aforesaid) was changed to 9 g and the revolution of T. K. Autohomomixer (as aforesaid) to 3200 r.p.m., the operation was made in the same manner as in Example 1 to give a fenitrothion microcapsule slurry having an active ingredient concentration of 20 wt. %. (Composition 1-2).

The resulting microcapsules having polyurethane wall had an average particle diameter of 50 μm, a wall thickness of 0.32 μm, and a value of the average particle diameter/wall thickness of 156.

EXAMPLE 3

Except that the amount of SUMIDUR L ® (as aforesaid) was changed to 4 g and the revolution of T. K. Autohomomixer (as aforesaid) to 3400 r.p.m., the operation was made in the same manner as in Example 1 to give a fenitrothion microcapsule slurry having an active ingredient concentration of 20 wt. %. (Composition 1-3).

The resulting microcapsules having polyurethane wall had an average particle diameter of 45 μm, a wall thickness of 0.13 μm, and a value of the average particle diameter/wall thickness of 346.

EXAMPLE 4

Except that the amount of SUMIDUR L ® (as aforesaid) was changed to 10 g and the revolution of T. K. Autohomomixer (as aforesaid) to 5600 r.p.m., the operation was made as in Example 1 to give a fenitrothion microcapsule slurry having an active ingredient concentration of 20 wt. %. (Composition 1-4).

The resulting microcapsules having polyurethane wall had an average particle diameter of 20 μm, a wall thickness of 0.14 μm, and a value of the average particle diameter/wall thickness of 143.

EXAMPLE 5

Except that the amount of SUMIDUR L ® (as aforesaid) was changed to 15 g and the revolution of T. K. Autohomomixer (as aforesaid) to 7200 r.p.m., the operation was made in the same manner as in Example 1 to give a fenitrothion microcapsule slurry having an active ingredient concentration of 20 wt. %. (Composition 1-5).

The resulting microcapsules having polyurethane wall had an average particle diameter of 12 μm, a wall thickness of 0.13 μm, and a value of the average particle diameter/wall thickness of 92.

EXAMPLE 6

Except that the amount of SUMIDUR L ® (as aforesaid) was changed to 8 g and the revolution of T. K. Autohomomixer (as aforesaid) to 5600 r.p.m., the operation was made in the same manner as in Example 1 to give a fenitrothion microcapsule slurry having an active ingredient concentration of 20 wt. %. (Composition 1-6).

The resulting microcapsules having polyurethane wall had an average particle diameter of 20 μm, a wall thickness of 0.11 μm, and a value of the average particle diameter/wall thickness of 182.

EXAMPLE 7

Except that the amount of SUMIDUR L ® (as aforesaid) was changed to 15 g and the revolution of T. K. Autohomomixer (as aforesaid) to 5600 r.p.m., the operation was made in the same manner as in Example 1 to give a fenitrothion microcapsule slurry having an active ingredient concentration of 20 wt. %. (Composition 1-7).

The resulting microcapsules having polyurethane wall had an average particle diameter of 20 μm, a wall thickness of 0.21 μm, and a value of the average particle diameter/wall thickness of 95.

EXAMPLE 8

Except that the amount of SUMIDUR L ® (as aforesaid) was changed to 60 g, the revolution of T. K. Autohomomixer (as aforesaid) to 6000 r.p.m., and the amount of ethylene glycol to 10 g, the operation was made in the same manner as in Example 1 to give a fenitrothion microcapsule slurry having an active ingredient concentration of 20 wt. %. (Composition 1-8).

The resulting microcapsules having polyurethane wall had an average particle diameter of 20 μm, a wall thickness of 0.79 μm, and a value of the average particle diameter/wall thickness of 25.

EXAMPLE 9

Except that SUMIDUR L ® (as aforesaid) (8 g) and toluene diisocyanate (SUMIDUR T80 ®; made by Sumitomo-Bayer Urethane Co., Ltd.) (1 g) were used instead of the sole use of SUMIDUR L ® (as aforesaid), the revolution of T. K. Autohomomixer (as aforesaid) was changed to 4500 r.p.m., the amount of the ethylene glycol to 8 g, and the stirring period of time in the constant temperature bath to 20 hours, the operation was made in the same manner as in Example 1 to give a fenitrothion microcapsule slurry having an active ingredient concentration of 20 wt. %. (Composition 1-9).

The resulting microcapsules having polyurethane wall had an average particle diameter of 30 μm, a wall thickness of 0.20 μm, and a value of the average particle diameter/wall thickness of 150.

EXAMPLE 10

SUMIDUR L ® (as aforesaid) (9 g) was added to fenitrothion (200 g), and the mixture was stirred to make an even solution. The resulting solution was added to an aqueous solution (400 g) containing 10 wt. % polyvinyl alcohol as a dispersing agent and the mixture was stirred at room temperature with T. K. Autohomomixer (as aforesaid) for several minutes until it became microdrops. The revolution at that time was 1200 r.p.m. Then, after adding ethylene glycol (7 g) to the dispersion, the contents were allowed to react in a constant temperature bath at 60° C. for 24 hours while slowly stirring to produce a suspension of microencapsulated product. The resulting product was incorporated with water to adjust the whole weight to 1000 g, after which the suspension was further diluted two-fold with a solution containing xanthan gum (0.3 wt. %) and magnesium aluminium silicate (0.6 wt. %) as a thickening agent to give a fenitrothion microcapsule slurry having an active ingredient concentration of 10 wt. %. (Composition 1-10).

The resulting microcapsules having polyurethane wall had an average particle diameter of 50 μm, a wall thickness of 0.32 μm, and a value of the average particle diameter/wall thickness of 156.

EXAMPLE 11

SUMIDUR N ® (as aforesaid) (10 g) was added to fenitrothion (200 g), and the mixture was stirred to make an even solution. The resulting solution was added to an aqueous solution (350 g) containing gum arabic (6 wt. %) and propylene glycol (2 wt. %) and the mixture was stirred with T. K. Autohomomixer (as aforesaid) at room temperature for several minutes until it became microdrops. The revolution at that time was 5600 r.p.m. Then, the contents were allowed to react in a constant temperature bath at 70° C. for 36 hours while slowly stirring to produce a suspension of microencapsulated product. To the resulting suspension water was added to adjust the whole weight to 1000 g, which was further diluted two-fold with an aqueous 4 wt. % carboxymethylcellulose (CELLOGEN 3H ®; made by Daiichi Kogyo Seiyaku K.K.) solution to give a fenitrothion microcapsule slurry having an active ingredient concentration of 10 wt. %. (Composition 1-11).

The resulting microcapsules having polyurethane wall had an average particle diameter of 20 μm, a wall thickness of 0.15 μm, and a value of the average particle diameter/wall thickness of 133.

EXAMPLE 12

Except that the amount of SUMIDUR L ® (as aforesaid) was changed to 9 g, the organophosphorus insecticide to be used to cyanophos and the revolution of T. K. Autohomomixer (as aforesaid) to 3200 r.p.m., the operation was made in the same manner as in Example 1 to give a cyanophos microcapsule slurry having an active ingredient concentration of 20 wt. %. (Composition 1-12).

The resulting microcapsules having polyurethane wall had an average particle diameter of 50 μm, a wall thickness of 0.34 μm, and a value of the average particle diameter/wall thickness of 147.

EXAMPLE 13

SUMIDUR L ® (as aforesaid) (12 g) was added to fenitrothion (200 g), and the mixture was stirred until an even solution was obtained. The resulting solution was added to an aqueous solution (350 g) containing gum arabic (17.5 g) and ethylene glycol (5 g), and the mixture was stirred with T. K. Autohomomixer (as aforesaid) at room temperature for several minutes until it became microdrops. The revolution was 1800 r.p.m. When the resulting dispersion was allowed to react in a constant temperature bath at 65° C. for 20 hours while slowly stirring, there was produced a suspension of a microencapsulated product. To the resulting suspension, an aqueous solution containing xanthan gum (0.2 wt. %) and aluminium magnesium silicate (0.6 wt. %) was added to adjust the whole weight to 1000 g to give a fenitrothion microcapsule slurry having an active ingredient concentration of 20 wt. %. (Composition 1-13).

The resulting microcapsules having polyurethane wall had an average particle diameter of 80 μm, a wall thickness of 0.67 μm, and a value of the average particle diameter/wall thickness of 119.

EXAMPLE 14

SUMIDUR L ® (as aforesaid) (10 g) was added to fenitrothion (200 g) and the mixture was stirred until it became an even solution, which was then added to an aqueous solution (350 g) containing gum arabic (5 wt. %) as a dispersing agent, and the dispersion was stirred with T. K. Autohomomixer (as aforesaid) at room temperature for several minutes until it became microdrops. The revolution was 5200 r.p.m. Then, the resulting dispersion was allowed to react in a constant temperature bath at 60° C. while slowly stirring for 24 hours to produce a suspension of a microencapsulated product. The resulting product was incorporated with water to adjust the total weight to 1000 g to give a fenitrothion microcapsule slurry having an active ingredient concentration of 20 wt. %. (Composition 2-1).

The resulting microcapsules having polyurea wall had an average particle diameter of 23 μm, a wall thickness of 0.15 μm, and a value of the average particle diameter/wall thickness of 153.

EXAMPLE 15

Except that the amount of SUMIDUR L ® (as aforesaid) was changed to 50 g and the revolution of T. K. Autohomomixer (as aforesaid) to 5300 r.p.m., the operation was made in the same manner as in Example 14 to give a fenitrothion microcapsule slurry having an active ingredient concentration of 20 wt. %. (Composition 2-2).

The resulting microcapsules having polyurea wall had an average particle diameter of 21 μm, a wall thickness of 0.64 μm, and a value of the average particle diameter/wall thickness of 33.

EXAMPLE 16

Except that the amount of SUMIDUR L ® (as aforesaid) was changed to 20 g and the revolution of T. K. Autohomomixer (as aforesaid) to 2000 r.p.m., the operation was made in the same manner as in Example 14 to give a fenitrothion microcapsule slurry having an active ingredient concentration of 20 wt. %. (Composition 2-3).

The resulting microcapsules having polyurea wall had an average particle diameter of 75 μm, a wall thickness of 0.95 μm, and a value of the average particle diameter/wall thickness of 79.

EXAMPLE 17

Except that the amount of SUMIDUR L ® (as aforesaid) was changed to 40 g and the revolution of T. K. Autohomomixer (as aforesaid) to 3400 r.p.m., the operation was made in the same manner as in Example 14 to give a fenitrothion microcapsule slurry having an active ingredient concentration of 20 wt. %. (Composition 2-4).

The resulting microcapsules having polyurea wall had an average particle diameter of 44 μm, a wall thickness of 109 μm, and a value of the average particle diameter/wall thickness of 40.

EXAMPLE 18

SUMIDUR L ® (as aforesaid) (5 g) was added to fenitrothion (200 g), and the mixture was stirred until an even solution was obtained. The resulting solution was added to an aqueous solution (350 g) containing gum arabic (5 wt. %) as a dispersing agent, and the mixture was stirred with T. K. Autohomomixer (as aforesaid) at room temperature for several minutes until it became microdrops. The revolution then was 3100 r.p.m. Then, after adding ethylenediamine (10 g) to the reaction system, the dispersion was allowed to react in a constant temperature bath at 60° C. for 24 hours while slowly stirring to produce a suspension of a microcapsulated product. To the resulting suspension, an aqueous solution of 1N HCl was added to adjust the pH of the system to 7, after which water was added to adjust the whole weight to 1000 g to give a fenitrothion microcapsule slurry having an active ingredient concentration of 20 wt. %. (Composition 2-5).

The resulting microcapsules having polyurea wall had an average particle diameter of 50 μm, a wall thickness of 0.20 μm, and a value of the average particle diameter/wall thickness of 250.

EXAMPLE 19

SUMIDUR N ® (as aforesaid) (10 g) was added to fenitrothion (200 g) and the mixture was stirred until it became an even solution, which was then added to an aqueous solution (350 g) containing gum arabic (5 wt. %) as a dispersing agent, and the mixture was stirred with T. K. Autohomomixer (as aforesaid) at room temperature for several minutes until it became microdrops. The revolution then was 5500 r.p.m. Then after adding phenylpenediamine (10 g) to the reaction system, the resulting dispersion was allowed to react in a constant temperature bath at 70° C. while slowly stirring for 36 hours to produce a suspension of a microencapsulated product. To the resulting suspension an aqueous solution of 0.1N HCl was added to neutralize it to pH 7, after which the suspension was incorporated with water to adjust the whole weight to 1000 g, and further the suspension was diluted two-fold with an aqueous 4 wt. % carboxymethylcellulose (Celogen 3H ®; made by Daiichi Kogyo Seiyaku K.K.) solution to give a fenitrothion microcapsule slurry having an active ingredient concentration of 10 wt. %. (Composition 2-6).

The resulting microcapsules having polyurea wall had an average particle diameter of 21 μm, a wall thickness of 0.18 μm, and a value of the average particle diameter/wall thickness of 117.

EXAMPLE 20

Except that SUMIDUR L ® (as aforesaid) (8 g) and toluene isocyanate (SUMIDUR T80 ®; made by Sumitomo-Bayer Urethane Co., Ltd.) (1 g) were used instead of sole SUMIDUR L ® (as aforesaid), the revolution of T. K. Autohomomixer (as aforesaid) to 5300 r.p.m., and the stirring time in the constant temperature bath was made 20 hours, the operation was made in the same manner as in Example 14 to give a fenitrothion microcapsule slurry having an active ingredient concentration of 20 wt. %. (Composition 2-7).

The resulting microcapsules having polyurea wall had an average particle diameter of 22 μm, a wall thickness of 0.13 μm, and a value of the average particle diameter/wall thickness of 169.

EXAMPLE 21

SUMIDUR L ® (as aforesaid) (9 g) was added to fenitrothion (200 g) and the mixture was stirred to make an even solution, which was added to an aqueous solution (400 g) containing a 10 wt. % polyvinyl alcohol as a dispersing agent and the mixture was stirred with T. K. Autohomomixer (as aforesaid) at room temperature for several minutes until it became microdrops. The revolution then was 1200 r.p.m. When the mixture was allowed to react in a constant temperature bath at 60° C. for 24 hours while slowly stirring, a suspension of microencapsulated product was formed. To the resulting product, water was added to adjust the whole weight to 1000 g, which was diluted two-fold with a solution containing xanthan gum (0.3 wt. %) and magnesium aluminium silicate (0.6 wt. %) as thickening agents to give a fenitrothion microcapsule slurry having an active ingredient concentration of 10 wt. %. (Composition 2-8).

The resulting microcapsules having polyurea wall had an average particle diameter of 50 μm, a wall thickness of 0.29 μm, and a value of the average particle diameter/wall thickness of 172.

EXAMPLE 22

SUMIDUR L ® (as aforesaid) (5 g) and fenitrothion (200 g) were mixed into an even solution, which was then added to an aqueous solution (350 g) containing gum arabic (17.5 g) and ethylenediamine (12 g), and the mixture was stirred with T. K. Autohomomixer (as aforesaid) at room temperature for several minutes until it became microdrops. The revolution then was 3100 r.p.m. Then , the dispersion was slowly stirred in a constant temperature bath at 50° C. for 20 hours t produce a suspension of microencapsulated product. To this, an aqueous solution of 1N HCl was added to adjust the pH in the system to 7, and then water was added to adjust the whole weight to 1000 g to give a fenitrothion microcapsule slurry having an active ingredient concentration of 20 wt. %. (Composition 2-9).

The resulting microcapsules having polyurea wall had an average particle diameter of 50 μm, a wall thickness of 0.2 μm, and a value of the average particle diameter/wall thickness of 250.

COMPARATIVE EXAMPLE 1

Except that the amount of SUMIDUR L ® (as aforesaid) was changed to 2.2 g and the revolution of T. K. Autohomomixer (as aforesaid) to 3400 r.p.m., the operation was made in the same manner as in Example 1 to give a fenitrothion microcapsule slurry having an active ingredient concentration of 20 wt. %. (Comparative composition 1).

The resulting microcapsules having polyurethane wall had an average particle diameter of 45 μm, a wall thickness of 0.07 μm, and a value of the average particle diameter/wall thickness of 643.

COMPARATIVE EXAMPLE 2

Except that the amount of SUMIDUR L ® (as aforesaid) was changed to 60 g, the revolution of T. K. Autohomomixer to 3200 r.p.m., and the amount of ethylene glycol to 10 g, the operation was made in the same manner as in Example 1 to give a fenitrothion microcapsule slurry having an active ingredient concentration of 20 wt. %. (Comparative composition 2).

The resulting microcapsules having polyurethane wall had an average particle diameter of 50 μm, a wall thickness of 1.98 μm, and a value of the average particle diameter/wall thickness of 25.

COMPARATIVE EXAMPLE 3

Except that the amount of SUMIDUR L ® (as aforesaid) was changed to 2.4 g and the revolution of T. K. Autohomomixer (as aforesaid) to 120 r.p.m., the operation was made in the same manner as in Example 1 to give a fenitrothion microcapsule slurry having an active ingredient concentration of 20 wt. %. (Comparative composition 3).

The resulting microcapsules having polyurethane wall had an average particle diameter of 100 μm, a wall thickness of 0.17 μm, and a value of the average particle diameter/wall thickness of 588.

COMPARATIVE EXAMPLE 4

Except that the amount of SUMIDUR L ® (as aforesaid) was changed to 3 g and the revolution of T. K. Autohomomixer (as aforesaid) to 4500 r.p.m., the operation was made in the same manner as in Example 14 to give a fenitrothion microcapsule slurry having an active ingredient concentration of 20 wt. %. (Comparative composition 4).

The resulting microcapsules having polyurea wall had an average particle diameter of 30 μm, a wall thickness of 0.06 μm, and a value of the average particle diameter/wall thickness of 500.

COMPARATIVE EXAMPLE 5

Except that the amount of SUMIDUR L ® (as aforesaid) was changed to 4 g and the revolution of T. K. Autohomomixer (as aforesaid) to 1000 r.p.m., the operation was made in the same manner as in Example 14 to give a fenitrothion microcapsule slurry having an active ingredient concentration of 20 wt. %. (Comparative composition 5).

The resulting microcapsules having polyurea wall had an average particle diameter of 100 μm, a wall thickness of 0.26 μm, and a value of the average particle diameter/wall thickness of 385.

COMPARATIVE EXAMPLE 6

Except that the amount of SUMIDUR L ® (as aforesaid) was changed to 140 g and the revolution of T. K. Autohomomixer (as aforesaid) to 2400 r.p.m., the operation was made in the same manner as in Example 14 to give a fenitrothion microcapsule slurry having an active ingredient concentration of 20 wt. %. (Comparative composition 6).

The resulting microcapsules having polyurea wall had an average particle diameter of 70 μm, a wall thickness of 5.42 μm, and a value of the average particle diameter/wall thickness of 13.

TEST EXAMPLE 1

(Primary Test)

Over a plywood board of 15×15 cm size, an aqueous dilution of the test composition (5 ml) was sprayed from the distance of 60 cm in height with a spray gun. The jet pressure of the spray gun was 0.6 kg/cm$^2$. After drying the board, 26 worker termites (*Coptotermes formosanus* Shiraki) were inoculated on the treated surface under the conditions of 25° C. and relative humidity 100 %, and the mortality after 24 hours was observed. After the completion of the test, the treated plywood board was kept under 40° C., and the termicidal activities of the treated surface were examined 1, 3 and 6 months later, respectively. The tests were replicated 5 times.

| Test compositions | Average particle diameter (μm) | Wall thickness (μm) | Average particle diameter / wall thickness | Treatment concentration of active ingredient (%) | Mortality (%) after 24 hours at the indicated months after treatment | | | |
|---|---|---|---|---|---|---|---|---|
| | | | | | 0 | 1 | 3 | 6 |
| Present composition 1-1 | 80 | 0.67 | 119 | 0.1 | 100 | 100 | 100 | 100 |
| Present composition 1-2 | 50 | 0.32 | 156 | 0.1 | 100 | 100 | 100 | 100 |
| Present composition 1-3 | 45 | 0.13 | 346 | 0.1 | 100 | 100 | 100 | 98 |
| Present composition 1-4 | 20 | 0.14 | 143 | 0.1 | 100 | 100 | 100 | 100 |
| Present composition 1-5 | 12 | 0.13 | 92 | 0.1 | 100 | 100 | 100 | 100 |
| Present composition 1-6 | 20 | 0.11 | 182 | 0.1 | 100 | 100 | 100 | 100 |
| Present composition 1-7 | 20 | 0.21 | 95 | 0.1 | 100 | 100 | 100 | 100 |
| Present composition 1-8 | 20 | 0.79 | 25 | 0.1 | 100 | 100 | 100 | 100 |
| Comparative composition 1 | 45 | 0.07 | 643 | 0.1 | 100 | 90 | 68 | 14 |
| Comparative composition 2 | 50 | 1.98 | 25 | 0.1 | 53 | 70 | 60 | 43 |
| Comparative composition 3 | 100 | 0.17 | 588 | 0.1 | 100 | 78 | 15 | 0 |
| Present composition 2-1 | 23 | 0.15 | 153 | 0.1 | 100 | 100 | 100 | 100 |
| Present composition 2-2 | 21 | 0.64 | 33 | 0.1 | 100 | 100 | 100 | 100 |
| Present composition 2-3 | 75 | 0.95 | 79 | 0.1 | 100 | 100 | 100 | 100 |
| Present composition 2-4 | 44 | 1.09 | 40 | 0.1 | 100 | 100 | 100 | 100 |
| Present composition 2-5 | 50 | 0.20 | 250 | 0.1 | 100 | 100 | 100 | 100 |
| Comparative composition 4 | 30 | 0.06 | 500 | 0.1 | 100 | 100 | 87 | 63 |
| Comparative composition 6 | 70 | 5.42 | 13 | 0.1 | 70 | 83 | 75 | 78 |

TEST EXAMPLE 2

(Primary test)

An aqueous dilution of the test composition (10 ml) was added to sandy soil (400 g), and they were well mixed. Then, the treated soil (5 g) was evenly spread in a plastic Petri dish of 9 cm in diameter laid with a filter paper wetted with water. 20 worker termites (*Coptotermes formosanus* Shiraki) were innoculated on the treated soil, and mortality after 3 days was observed. The remaining treated soil was kept under 40° C., and after lapse of the prescribed period, a residual effect of the soil was assessed by the same bio-essay-method. The tests were repeated 3 times.

| Test compositions | Average particle diameter ($\mu$m) | Wall thickness ($\mu$m) | Average particle diameter Wall thickness | Treatment concentration of active ingredient (%) | Mortality (%) after 3 days at the indicated months after treatment | | | |
|---|---|---|---|---|---|---|---|---|
| | | | | | 0 | 1 | 3 | 6 |
| Present composition 2-1 | 23 | 0.15 | 153 | 0.5 | 100 | 100 | 100 | 100 |
| Present composition 2-2 | 21 | 0.64 | 33 | 0.5 | 100 | 100 | 100 | 100 |
| Comparative composition 4 | 30 | 0.06 | 500 | 0.5 | 100 | 87 | 18 | 0 |
| Comparative composition 5 | 100 | 0.26 | 385 | 0.5 | 100 | 96 | 0 | 0 |

TEST EXAMPLE 3

The present composition 1-4- was diluted by water (20 times), respectively. The aqueous dilution was sprayed on the surface of soil under a floor of a mortar-coated wooden house at the rate of 30 g/m$^2$ as fenitrothion. After 4 years, the damage under the floor by termites was checked. But there was no damage under the floor. At the same time, 30 g of the soil treated under the floor was taken from the surface of the soil and 10 g of the sampled soil was uniformly spread on a filter paper wetted with water in a Petri dish whose diameter was 9 cm. Then, 20 worker termites (*Coptotermes formosanus* Shiraki) were inoculated on the treated surface. It was kept for one day at 25° C. under the condition of 100 % of relative humidity and motality observed. The test was repeated three times. As a result, the motality was 100 % in every repeat.

What is claimed is:

1. A method for preventing termites by applying 5–100 g of at least one organophosphorus insecticidal compound per m$^2$ to a soil surface under a floor of a building, a foundation, etc., at least one of said compounds being encapsulated in a microcapsule having a polyurethane or polyurea wall, said microcapsule having an average particle diameter of not more than 80$\mu$m, a wall thickness of 0.1–1 $\mu$m, and a value of the average particle diameter/wall thickness of 20–400.

2. A method according to claim 1 wherein the application amount of the compound is 20–40 g per m$^2$.

3. A method according to claim 1 wherein the microcapsule has a polyurethane wall.

4. A method according to claim 1 wherein the microcapsule has a polyurea wall.

5. A method according to claim 1 wherein the organophosphorus compound is fenitrothion.

6. A microencapsulated organophosphorus termite controlling composition comprising at least one of organophosphorus insecticidal compounds encapsulated in a microcapsule formed of a polyurea or polyurethane wall which has an average particle diameter of not more than 80 $\mu$m, a wall thickness of 0.1–1 $\mu$m, and a value of the average particle diameter/wall thickness of 20–400.

7. The termite controlling composition according to claim 6, wherein the microcapsule has a polyurethane wall.

8. The termite controlling composition according to claim 6, wherein the microcapsule has a polyurea wall.

9. The termite controlling composition according to claim 6, wherein the organophosphorus insecticidal compound is fenitrothion.

* * * * *